United States Patent
Shin et al.

(10) Patent No.: US 11,759,413 B2
(45) Date of Patent: Sep. 19, 2023

(54) SPRAY TYPE COSMETIC COMPOSITION HAVING MAKEUP-MAINTAINING ABILITY AND SPRAYING POWER

(71) Applicant: LG HOUSEHOLD & HEALTH CARE LTD., Seoul (KR)

(72) Inventors: Hyeok-Jun Shin, Seoul (KR); Moon-Ju Kim, Seoul (KR); Seo-Hee Jung, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 81 days.

(21) Appl. No.: 17/340,750

(22) Filed: Jun. 7, 2021

(65) Prior Publication Data

US 2021/0386648 A1 Dec. 16, 2021

(30) Foreign Application Priority Data

Jun. 15, 2020 (KR) .......... 10-2020-0072572
Nov. 5, 2020 (KR) .......... 10-2020-0147056

(51) Int. Cl.
*A61K 8/73* (2006.01)
*A61Q 1/00* (2006.01)
*A61K 8/04* (2006.01)
*A61K 8/81* (2006.01)

(52) U.S. Cl.
CPC .............. *A61K 8/732* (2013.01); *A61K 8/046* (2013.01); *A61K 8/8176* (2013.01); *A61Q 1/00* (2013.01)

(58) Field of Classification Search
None
See application file for complete search history.

(56) References Cited

U.S. PATENT DOCUMENTS 6,413,505 B1 7/2002 Vitale et al.

FOREIGN PATENT DOCUMENTS

| KR | 10-0670963 B1 | 1/2007 |
|---|---|---|
| KR | 10-1714598 B1 | 3/2017 |
| KR | 10-1716475 B1 | 3/2017 |
| KR | 10-2019-0002810 A | 1/2019 |
| KR | 10-2020-0046737 A | 5/2020 |

OTHER PUBLICATIONS

Lautenschlager. (Poly)Saccharides in cosmetics products—From alginate to xanthan gum. Kosmetische Praxis 2009 (4) 12-15 (Year: 2009).*

* cited by examiner

*Primary Examiner* — Nicole P Babson
(74) *Attorney, Agent, or Firm* — Birch, Stewart, Kolasch & Birch, LLP

(57) ABSTRACT

This disclosure provides a spray type cosmetic composition comprising hydroxypropyl starch (HPS) and polyvinylpyrrolidone (PVP). In more detail, this disclosure provides a spray-type cosmetic composition for makeup fixer, comprising HPS and PVP, which has excellent properties such as makeup maintaining ability, spraying power, and less stickiness at the same time.

12 Claims, 2 Drawing Sheets

[Figure 1]
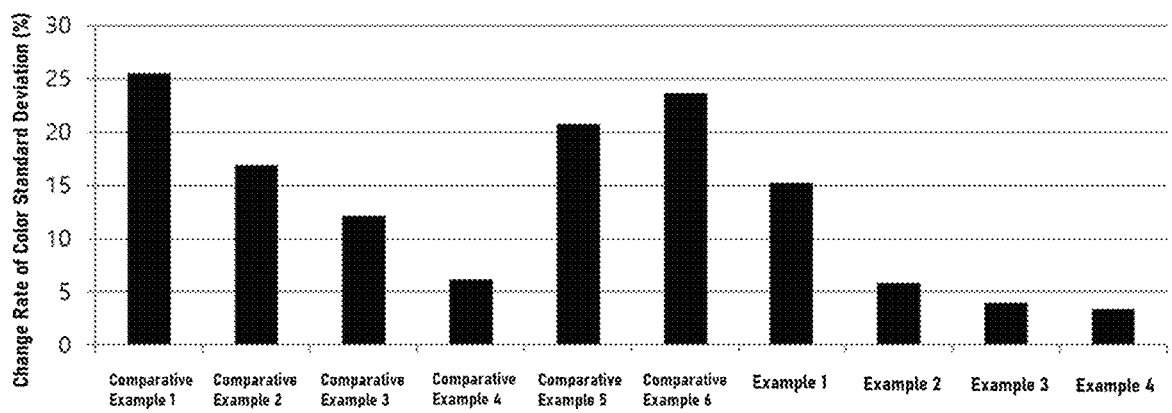
[Figure 2]
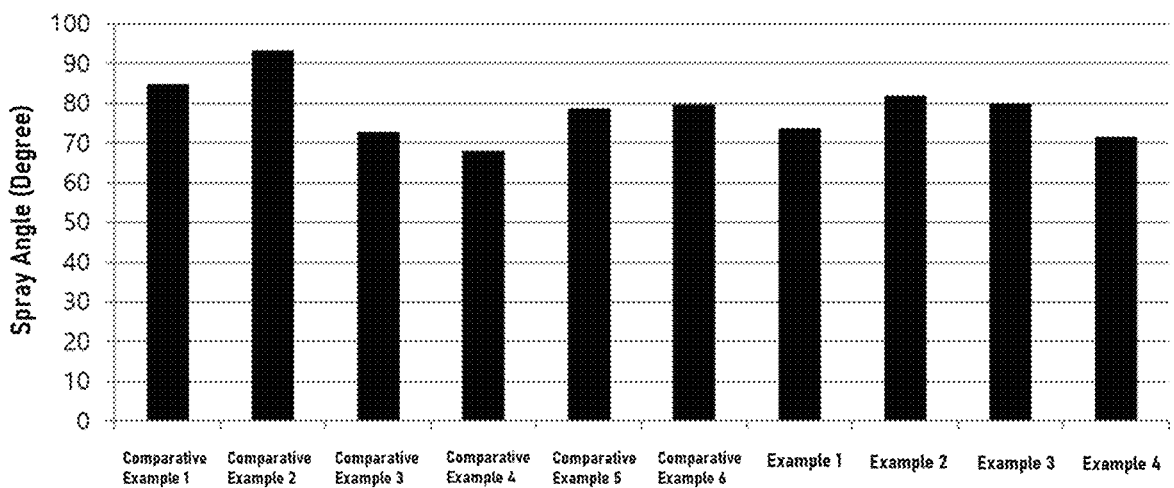

[Figure 3]
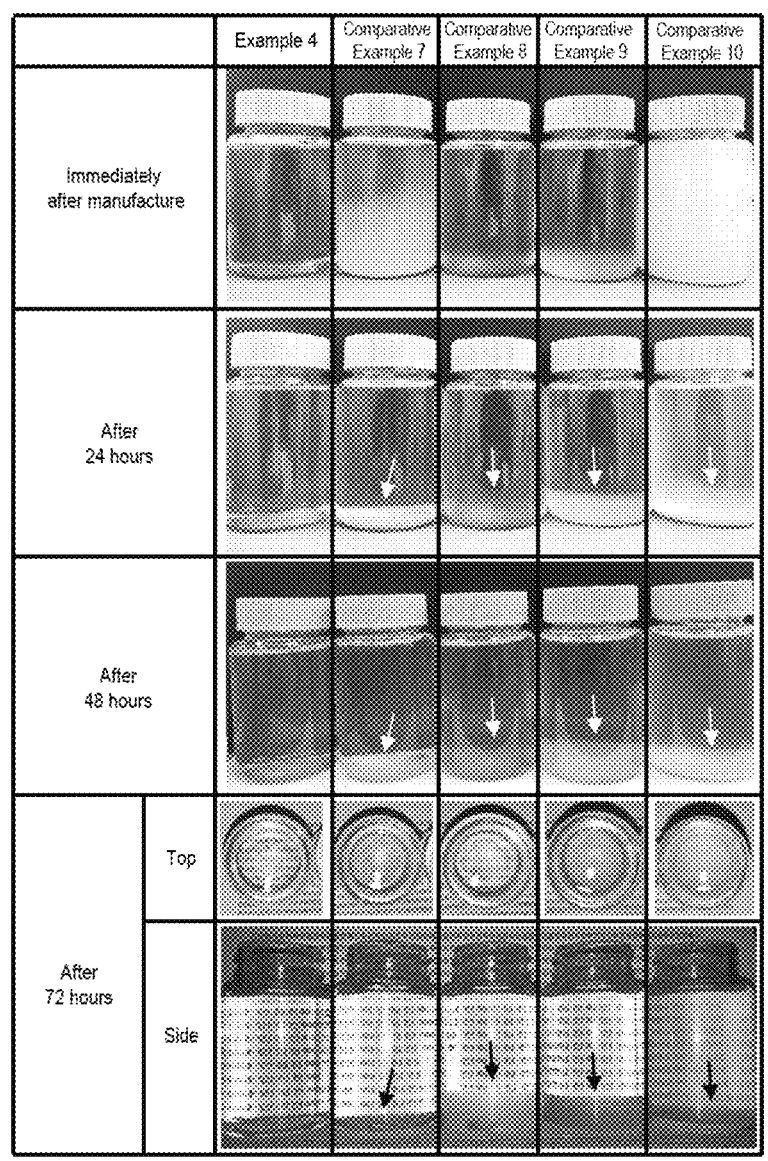

SPRAY TYPE COSMETIC COMPOSITION HAVING MAKEUP-MAINTAINING ABILITY AND SPRAYING POWER

TECHNICAL FIELD

This application claims priority to Patent Application No. 10-2020-0072572 filed in Republic of Korea on Jun. 15, 2020 and Patent Application No. 10-2020-0147056 filed in Republic of Korea on Nov. 5, 2020, the entire contents of which are incorporated herein by reference.

The present invention relates to a spray type cosmetic composition having excellent makeup maintaining ability and spraying power at the same time. More specifically, the present invention relates to a fixer cosmetic composition used after application of makeup cosmetics, and in particular, to a fixer cosmetic composition in a mist formulation.

BACKGROUND ART

The film forming agent used in cosmetics is a polymeric compound mainly in the form of a polymer, and plays a role of forming a flexible, durable, and adherent film on the surface of the skin or hair.

Films having different properties may be formed through various synthesis or reaction processes of the film forming agents. Film forming agents are mainly used in color eye makeup cosmetics (Korean Patent Publication No. 10-2019-0002810), and also used in fundamental cosmetics for purposes such as wrinkle improvement (Korean Patent No. 10-1714598), and peel-off pack (Korean Patent No. 10-1716475). However, the more the film-forming agent is used, the more sticky it is and the spraying power decreases.

On the other hand, among fundamental cosmetics, mist is classified as leave-on cosmetics that are sprayed on the skin surface and remain in a large area.

Among these mist cosmetics, a fixer that is used after color makeup and enhances makeup lasting power is being released.

In the makeup fixer, spraying power and makeup maintaining ability are important factors, but it is difficult to satisfy both of these at the same time. Therefore, there is a need for research to solve this problem.

DISCLOSURE

Technical Problem

A problem to be solved by this disclosure is to provide a spray type cosmetic composition having less stickiness and excellent makeup maintaining ability (fixing and/or lasting power) and spraying power at the same time.

Another problem to be solved by this disclosure is to provide a cosmetic composition that is a spray type formulation such as a mist formulation, its use is a makeup fixer, and has excellent makeup maintaining ability and spraying power at the same time.

Technical Solution

The present inventors attempted to develop a spray-type cosmetic composition containing a film-forming agent and having less stickiness and excellent spraying power in order to increase makeup fixing and lasting power.

To this end, a composition was prepared using polyvinylpyrrolidone having excellent adhesion property. Polyvinylpyrrolidone has the advantage of superior makeup lasting power compared to other film forming agents. However, as the content of polyvinylpyrrolidone increased to increase makeup fixing and lasting power, there was a disadvantage of being sticky and reducing spraying power.

In order to overcome the above problems caused by polyvinylpyrrolidone, the inventors of the present invention added various starch materials to the composition. Starch means a starch class polymer. Starch is an amphiphilic substance that absorbs water and oil at the same time and has a film-forming function. In starch class polymer, there are hydroxypropyl starch phosphate, acetylated corn starch, acetylated rice starch, and the like, which have undergone various modifications or synthesis in order to increase solubility.

As a result of confirming by the present inventors, when hydroxypropyl starch among starch materials is included in the fixer composition together with polyvinylpyrrolidone, the advantages of the polyvinylpyrrolidone are maintained (i.e., makeup fixing power and lasting power are maintained), the disadvantage of polyvinylpyrrolidone, the reduction in spraying power, was insignificant, and at the same time, it was not sticky.

Not all starch materials exhibited the above effects, and only hydroxypropyl starch was suitable for its intended use. In particular, in the case of using non-modified starch and modified general starch, not hydroxypropyl starch, it showed poor results in terms of precipitation stability of the formulation.

That is, the inventors of the present invention address the limitations of low makeup lasting power, low mist spraying power, or stickiness that occur when each of polyvinylpyrrolidone and hydroxypropyl starch is used alone. When combining polyvinylpyrrolidone and hydroxypropyl starch, the makeup fixing and lasting power of polyvinylpyrrolidone and the spraying power and less stickiness of hydroxypropyl starch can be simultaneously maintained (without affecting each other in negative directions), by which the present invention was completed.

One embodiment of the present disclosure provides a spray type cosmetic composition comprising hydroxypropyl starch (HPS) and polyvinylpyrrolidone (PVP), and used after application of a makeup cosmetic. That is, the spray type cosmetic composition according to the present disclosure can be used by spraying on it after applying makeup.

In a preferred embodiment of the present disclosure, the composition according to an embodiment of the present disclosure is used as a makeup fixer, having excellent makeup maintaining ability and spraying power at the same time.

The spray type cosmetic composition according to the present disclosure comprises hydroxypropyl starch. In the present invention, hydroxypropyl starch is preferred because of its excellent film-forming ability, high dispersion stability, and good formulation stability. On the other hand, among commonly used starches, unmodified starches (e.g., corn starch, etc.) may be undesirable due to their low dispersion maintaining ability in a liquid type formulation. In addition, modified starches other than hydroxypropyl starch may be undesirable in terms of precipitation stability of the formulation.

In one embodiment of the present disclosure, the hydroxypropyl starch is comprised in an amount of 0.1 to 5% by weight, preferably 0.3 to 2% by weight, based on the total weight of the composition.

The spray type cosmetic composition according to the present disclosure comprises polyvinylpyrrolidone, and the polyvinylpyrrolidone may be a polymer of N-vinyl-2-pyrrolidone.

Preferably, polyvinylpyrrolidone having a weight average molecular weight of 1,000 to 5,000,000 g/mol may be used as the polyvinylpyrrolidone according to the present disclosure. More preferably, polyvinylpyrrolidone having a weight average molecular weight of 40,000 to 80,000 g/mol may be used as the polyvinylpyrrolidone according to the present disclosure.

In one embodiment of the present disclosure, as the polyvinylpyrrolidone, for example, ASHLAND's PVP K-30 may be used.

In one embodiment of the present disclosure, the polyvinylpyrrolidone is comprised in an amount of 0.1 to 5% by weight, preferably 0.5 to 4% by weight, based on the total weight of the composition.

In one embodiment of the present disclosure, the hydroxypropyl starch is comprised in an amount of 0.1 to 5% by weight based on the total weight of the composition, and the polyvinylpyrrolidone is comprised in 0.1 to 5% by weight based on the total weight of the composition.

In one embodiment of the present disclosure, the composition according to the present invention comprises hydroxypropyl starch and polyvinylpyrrolidone in a weight ratio of 0.1:1 to 10:1, preferably in a weight ratio of 1:1 to 1:6 (hydroxypropyl starch:polyvinylpyrrolidone).

In the present disclosure, the term "spray-type formulation" may mean a formulation such as aerosol, mist, or spray, but is not limited thereto. Preferably, in the present disclosure, the spray-type formulation may be a mist formulation. That is, the composition according to the present disclosure may be applied to the skin as a spray, aerosol or mist formulation, preferably a mist formulation.

In one embodiment of the present disclosure, the composition according to the present disclosure may further comprises a surfactant. This surfactant may help in the solubilization of other ingredients comprised in the composition.

The surfactants that may be comprised in the spray type cosmetic composition according to an embodiment of the present disclosure include polysorbate 20 (Tween 20), sorbitan isostearate, sorbitan stearate, and polyethylene glycol (PEG)-40 hydrogenated castor oil, PEG-60 hydrogenated castor oil, and the like may be used, but are not limited thereto.

In one embodiment of the present disclosure, the surfactant is comprised in an amount of, for example, 0.1 to 5% by weight, more preferably 0.5 to 3% by weight, based on the total weight of the composition.

The spray type cosmetic composition according to the present disclosure may further comprise a solvent or a drying rate increasing agent. As such a solvent or a drying rate increasing agent, for example, purified water, ethanol, or a mixed solvent thereof may be used, but the present invention is not limited thereto. In a preferred embodiment of the present disclosure, the solvent or drying rate increasing agent according to the present disclosure is a mixed solvent of purified water and ethanol, of which ethanol is comprised in an amount of 1 to 20% by weight, more preferably 5 to 15% by weight based on the total weight of the composition. Purified water forms the remaining amount excluding the above-mentioned ingredients and optional ingredients described later.

In this disclosure, the spray-type cosmetic composition according to this disclosure may further comprise all kinds of excipients that can be used in ordinary cosmetics, such as preservatives, fragrances, antioxidants, moisturizers, dispersants, pH adjusters, astringents, pigments and the like, in addition to the aforementioned ingredients. These can be commercially purchased and used.

The preservatives that may be comprised in the spray type cosmetic composition according to the present disclosure may include phenoxyethanol, methylparaben, ethylparaben, propylparaben, butylparaben, benzyl alcohol, sodium benzoate, etc., but are not limited thereto.

In another embodiment of the present disclosure, the spray type cosmetic composition according to the present disclosure comprises 0.1 to 5% by weight of hydroxypropyl starch; 0.1 to 5% by weight of polyvinylpyrrolidone; 0.1 to 5% by weight of preservatives, surfactants, fragrances or mixtures thereof; and a residual amount of a solvent or a drying speed increasing agent, based on the total weight of the composition.

This disclosure also relates to the cosmetic use (method) of the aforementioned cosmetic composition(s) according to this disclosure.

That is, another embodiment of the present disclosure provides a method of fixing or holding a makeup, comprising spraying a spray-type cosmetic composition comprising hydroxypropyl starch and polyvinylpyrrolidone onto a subject in need of maintenance of makeup.

As the cosmetic composition used in the method of the present disclosure, the cosmetic compositions of the present disclosure mentioned above are used.

All the ingredients described in the present invention do not exceed the maximum use amount stipulated by related laws and regulations, preferably such as Korea, China, the United States, Europe, Japan, etc. (e.g., regulations on cosmetic safety standards (Korea), cosmetic safety technical standards (China), the hygiene norms (China)). That is, preferably, the cosmetic composition according to the present invention, or the composition for personal care, comprises the ingredients according to the present invention to the limit of the content allowed by the relevant laws and norms of each country.

Advantageous Effects

This disclosure provides a spray type cosmetic composition with excellent makeup maintaining ability and spraying power at the same time. More specifically, the spray type cosmetic composition of the present disclosure adds hydroxypropyl starch so that the spray angle does not decrease while increasing the makeup maintaining ability as the content of polyvinylpyrrolidone increases. Due to this combination, the composition of this disclosure not only further improves the makeup maintaining ability, but also reduces the reduction in spray angle.

BRIEF DESCRIPTION OF DRAWINGS

FIG. 1 is a graph showing the rate of change in color standard deviation of Examples 1 to 4 and Comparative Examples 1 to 6.

FIG. 2 is a graph showing the mist spray angles of Examples 1 to 4 and Comparative Examples 1 to 6.

FIG. 3 shows the result of precipitation of Example 4 and Comparative Examples 7 to 10. Arrows indicate sedimentation.

MODE FOR INVENTION

The present invention will be described in more detail based on the following examples, but this is not intended to limit the scope of the present invention. In addition, those of ordinary skill in the art will be able to add various modifications and variations to the present invention within the scope not detrimental to the spirit of the present invention.

Preparation Example 1: Preparation of Spray Type Cosmetic Composition

Polyvinylpyrrolidone and hydroxypropyl starch were added to the aqueous phase by a dispersion process, and the fragrance was solubilized and added to prepare a spray type cosmetic composition (Examples 1 to 4).

As a comparison group, a spray-type cosmetic composition without hydroxypropyl starch and polyvinylpyrrolidone (Comparative Example 1), spray-type cosmetic compositions without hydroxypropyl starch (Comparative Examples 2 to 4), and spray type cosmetic compositions without polyvinylpyrrolidone (Comparative Examples 5 to 6) were prepared in the same process.

Experiment Method
1) After ingredient 1 (purified water) was heated to 60° C., ingredients 2 to 3 were gradually added and dispersed with a disper for 30 minutes.
2) Ingredients 5 to 9 were added to ingredient 4 and completely dissolved at 50° C.
3) The resultant of item 2) was slowly added to the resultant of item 1) with a dropper, and mixed at 150 RPM for 10 minutes.

3) After 10 minutes, the color standard deviation of the pixels on the left and right sides of the face photographed by the facial photographic analysis system was measured.
4) After 4 hours, the color standard deviation of the pixels on the left and right sides of the face photographed by the facial photographing analysis system was measured in the same manner.
5) Relative comparison was made by calculating the rate of change of color standard deviation using an equation:

(Rate of change=(Standard deviation of color after 4 hours−Standard deviation of color after 10 minutes)/Standard deviation of color after 10 minutes)

The results are shown in FIG. 1. It was determined that uniform makeup was maintained as the color standard deviation ratio in the unit area was smaller. Looking at the color standard deviation change rate chart of Comparative Examples 2 to 4, it was confirmed that the higher the PVP content, the lower the color standard deviation change rate, so that the makeup maintaining ability increased. Looking at the color standard deviation change rate chart of Comparative Examples 5 to 6, it was confirmed that the makeup maintaining ability was lowered because the color standard deviation change rate increased when HPS was comprised. In Examples 2 to 4 comprising PVP and HPS at the same time, it was confirmed that the color standard deviation

TABLE 1

| | Ingredients | Comparative Example | | | | | | Example | | | |
|---|---|---|---|---|---|---|---|---|---|---|---|
| | | 1 | 2 | 3 | 4 | 5 | 6 | 1 | 2 | 3 | 4 |
| 1 | Purified Water | To 100 | To 100 | To 100 | To 100 | To 100 | To 100 | To 100 | To 100 | To 100 | To 100 |
| 2 | Polyvinylpyrrolidone (PVP) | — | 1 | 2 | 3 | — | — | 1 | 2 | 3 | 3 |
| 3 | Hydroxypropyl Starch (HPS) | — | — | — | — | 1 | 2 | 1 | 1 | 1 | 0.5 |
| 4 | Ethanol | 10 | 10 | 10 | 10 | 10 | 10 | 10 | 10 | 10 | 10 |
| 5 | Polysorbate 20 | 0.5 | 0.5 | 0.5 | 0.5 | 0.5 | 0.5 | 0.5 | 0.5 | 0.5 | 0.5 |
| 6 | Sorbitan isostearate | 0.6 | 0.6 | 0.6 | 0.6 | 0.6 | 0.6 | 0.6 | 0.6 | 0.6 | 0.6 |
| 7 | Phenoxyethanol | 0.3 | 0.3 | 0.3 | 0.3 | 0.3 | 0.3 | 0.3 | 0.3 | 0.3 | 0.3 |
| 8 | PEG-40 Hydrogenated Castor Oil | 1 | 1 | 1 | 1 | 1 | 1 | 1 | 1 | 1 | 1 |
| 9 | Fragrance | 0.1 | 0.1 | 0.1 | 0.1 | 0.1 | 0.1 | 0.1 | 0.1 | 0.1 | 0.1 |

In Table, as polyvinylpyrrolidone, ASHLAND's brand name PVP K-30 (molecular weight 40,000~80,000 g/mol) was used. The same ingredient was used in other preparation examples below.

Experimental Example 1: Evaluation of Makeup Maintaining Ability

For the compositions of Comparative Examples 1 to 6 and Examples 1 to 4, makeup maintaining ability was evaluated. The makeup maintaining ability on the skin surface was compared relative to the color standard deviation change rate, which is a measure of uniformity after a certain period of time.

Experiment Method
1) After evenly applying a general foundation on the skin surface, the spray type cosmetic composition was separated by 15 cm with a mist pump.
2) The composition was evenly sprayed on half of the face (3 times, 0.3 g).

change rate was decreased compared to Comparative Examples 1 to 6, so that the makeup maintaining ability was improved.

In conclusion, when PVP and HPS were comprised at the same time, a lower change rate of color standard deviation was observed compared to the use of PVP alone and the use of HPS alone. In other words, it was confirmed that the makeup maintaining ability was improved.

Experimental Example 2: Evaluation of Mist Spraying Power

For the compositions of Comparative Examples 1 to 6 and Examples 1 to 4, the mist spraying power was evaluated. The mist spraying power was compared relative to each other by measuring the spray angle.

Experiment Method
1) After filling the makeup fixing cosmetic composition in a general mist pump container, the sprayed image was photographed and the spray angle was measured.

The results are shown in FIG. 2. Looking at the spray angle charts of Comparative Examples 2 to 4, it was confirmed that the higher the PVP content, the lower the spray angle, and thus the fine spray power decreased. Looking at the spray angle charts of Comparative Examples 5 to 6, it was confirmed that the fine spraying power was maintained regardless of the HPS content. It was confirmed that Examples 1 to 4 comprising PVP and HPS at the same time increased the spraying angle than Comparative Examples 3 and 4, so that the fine spraying power was increased.

In conclusion, when the combination of HPS and PVP was used, the spray angle decreased compared to when 1% by weight of PVP was comprised alone. However, when the combination of HPS and PVP was used, the spray angle was superior to that of comprising 2% by weight of PVP. In particular, it was confirmed that when using a combination of HPS and PVP, a level equivalent to about 70 degrees of spray angle that consumers can feel can be achieved.

However, although the spray angle of Example 4 was slightly lower than that of Example 3, the quality was more excellent in terms of formulation stability and feeling of use.

TABLE 2

|  | Example 1 | Example 2 | Example 3 | Example 4 |
|---|---|---|---|---|
| Sedimentation | Δ | Δ | Δ | Δ |
| Redispersion | Δ | Δ | Δ | O |

(Evaluation criteria: O-good, Δ-slightly unstable, X-unstable)

Preparation Example 2: Preparation of Spray Type Cosmetic Composition

As a comparative group, spray type cosmetic compositions (Comparative Examples 7 to 10) each including four types of unmodified and modified starch excluding hydroxypropyl starch were prepared in the same process as in Preparation Example 1.

Experiment Method

1) After ingredient 1 (purified water) was heated to 60° C., ingredients 2 to 7 were gradually added and dispersed with a disper for 30 minutes.

2) Ingredients 9 to 13 were added to ingredient 8 and completely dissolved at 50° C.

3) The resultant of item 2) was slowly added to the resultant of item 1) with a dropper, lit and mixed at 150 RPM for 10 minutes.

TABLE 3

|  |  | Comparative Example | | | |
|---|---|---|---|---|---|
|  | Ingredient | 7 | 8 | 9 | 10 |
| 1 | Purified Water | To 100 | To 100 | To 100 | To 100 |
| 2 | Polyvinylpyrrolidone (PVP) | 3 | 3 | 3 | 3 |
| 3 | Corn starch | 0.5 | — | — | — |
| 4 | Sodium carboxymethyl starch | — | 0.5 | — | — |
| 5 | Hydroxypropyl starch phosphate | — | — | 0.5 | — |
| 6 | Dimethylimidazolidinone rice starch | — | — | — | 0.5 |
| 7 | Hydroxypropyl Starch (HPS) | — | — | — | — |
| 8 | Ethanol | 10 | 10 | 10 | 10 |
| 9 | Polysorbate 20 | 0.5 | 0.5 | 0.5 | 0.5 |
| 10 | Sorbitan isostearate | 0.6 | 0.6 | 0.6 | 0.6 |
| 11 | Phenoxyethanol | 0.3 | 0.3 | 0.3 | 0.3 |
| 12 | PEG-40 Hydrogenated Castor Oil | 1 | 1 | 1 | 1 |
| 13 | Fragrance | 0.1 | 0.1 | 0.1 | 0.1 |

Experimental Example 3: Evaluation of Stability Over Time

The composition of Examples 1 to 4 was evaluated for stability over time. The stability over time was confirmed by the sedimentation and redispersion scale.

Experiment Method

1) The spray type cosmetic composition was frozen for 3 days at low temperature (−20° C.), then melted and redispersed.

2) The above process was repeated 5 times to visually check the sedimentation and redispersibility.

The results are shown in Table 2 below. It was confirmed that Examples 1 to 3 comprising 1% by weight of HPS had a relatively lower degree of redispersion than Example 4 containing 0.5% by weight of HPS.

In conclusion, it was confirmed that the lower the HPS content, the higher the redispersability was.

Experimental Example 4: Starch Stability Evaluation 100 mL of the prepared Comparative Examples and Example were allowed to stand at room temperature for 48 hours to confirm the presence or absence of sedimentation.

As a result, it was confirmed that the four types of unmodified and modified starch other than hydroxypropyl starch have poor dispersion stability because sedimentation occurs (Table 4 and FIG. 3).

TABLE 4

|  | Comparative Example 7 | Comparative Example 8 | Comparative Example 9 | Comparative Example 10 | Example 4 |
|---|---|---|---|---|---|
| Immediately after manufacturing | Suspension | Good | Good | Suspension | Good |
| After 24 hours | Sedimentation | Sedimentation | Sedimentation | Sedimentation | Good |
| After 48 hours | Sedimentation | Sedimentation | Sedimentation | Sedimentation | Good |
| After 72 hours | Sedimentation | Sedimentation | Sedimentation | Sedimentation | Good |

The invention claimed is:

1. A method for fixing or holding makeup, comprising spraying to a subject in need of maintenance of the makeup a spray-type cosmetic composition comprising hydroxypropyl starch and polyvinylpyrrolidone, wherein the content of hydroxypropyl starch in the composition is 0.1 to 5% by weight based on the total weight of the composition, and the content of polyvinylpyrrolidone is 0.1 to 5% by weight based on the total weight of the composition.

2. The method of claim 1, wherein the composition comprises hydroxypropyl starch and polyvinylpyrrolidone in a weight ratio of 0.1:1 to 10:1 (hydroxypropyl starch:polyvinylpyrrolidone).

3. The method of claim 1, wherein the spray-type cosmetic composition comprises hydroxypropyl starch and polyvinylpyrrolidone in a weight ratio of 1:1 to 1:6 (hydroxypropyl starch:polyvinylpyrrolidone).

4. The method of claim 1, wherein the polyvinylpyrrolidone has a weight average molecular weight of 1,000 to 5,000,000 g/mol.

5. The method of claim 1, wherein the polyvinylpyrrolidone has a weight average molecular weight of 40,000 to 80,000 g/mol.

6. The method of claim 1, wherein the polyvinylpyrrolidone is present in an amount of 0.5 to 4% by weight based on the total weight of the spray-type cosmetic composition.

7. The method of claim 1, further comprising 0.1 to 5% by weight of preservatives, surfactants, fragrances or mixtures thereof, based on the total weight of the spray-type cosmetic composition.

8. The method of claim 7, further comprising a solvent or a drying speed increasing agent.

9. The method of claim 1, wherein the spray-type cosmetic formulation is an aerosol, mist, or spray.

10. The method of claim 1, wherein the spray-type cosmetic formulation further comprises a surfactant in an amount of 0.1 to 5% by weight, based on the total weight of the composition.

11. The method of claim 10, wherein the surfactant is polysorbate 20 (Tween 20), sorbitan isostearate, sorbitan stearate, polyethylene glycol (PEG)-40 hydrogenated castor oil, or PEG-60 hydrogenated castor oil.

12. The method of claim 1, wherein the spray-type cosmetic formulation further comprises a drying rate increasing agent, a preservative, a fragrance, an antioxidant, a moisturizer, a dispersant, a pH adjuster, an astringent, or a pigment.

* * * * *